US011375976B2

(12) United States Patent
Cai

(10) Patent No.: US 11,375,976 B2
(45) Date of Patent: Jul. 5, 2022

(54) WIRELESS STETHOSCOPE FOR TRANSMITTING, RECORDING, STORING AND DIAGNOSTIC CAPABILITIES INCLUDING AN EARPIECE

(71) Applicant: John Jun Cai, Williamsville, NY (US)

(72) Inventor: John Jun Cai, Williamsville, NY (US)

(*) Notice: Subject to any disclaimer, the term of this patent is extended or adjusted under 35 U.S.C. 154(b) by 846 days.

(21) Appl. No.: 16/180,832

(22) Filed: Nov. 5, 2018

(65) Prior Publication Data
US 2019/0133548 A1 May 9, 2019

Related U.S. Application Data

(60) Provisional application No. 62/581,392, filed on Nov. 3, 2017.

(51) Int. Cl.
| | |
|---|---|
| *A61B 7/04* | (2006.01) |
| *A61B 8/08* | (2006.01) |
| *A61B 5/00* | (2006.01) |
| *A61B 7/00* | (2006.01) |
| *A61B 8/00* | (2006.01) |
| *H04R 3/00* | (2006.01) |
| *H04R 19/04* | (2006.01) |

(Continued)

(52) U.S. Cl.
CPC .............. *A61B 7/04* (2013.01); *A61B 5/0022* (2013.01); *A61B 5/7282* (2013.01); *A61B 7/003* (2013.01); *A61B 8/4472* (2013.01); *A61B 8/462* (2013.01); *A61B 8/483* (2013.01); *A61B 8/486* (2013.01); *A61B 8/488* (2013.01); *A61B 8/565* (2013.01); *H04R 3/00* (2013.01); *A61B 5/002* (2013.01); *A61B 5/318* (2021.01); *A61B 2560/0214* (2013.01); *A61B 2562/0204* (2013.01); *A61B 2562/0247* (2013.01); *H04R 1/1041* (2013.01); *H04R 7/04* (2013.01); *H04R 19/04* (2013.01); *H04R 2420/07* (2013.01)

(58) Field of Classification Search
CPC ....................................................... A61B 7/04
See application file for complete search history.

(56) References Cited

U.S. PATENT DOCUMENTS

| | | |
|---|---|---|
| 6,533,736 B1 | 3/2003 | Moore |
| 7,520,860 B2 | 4/2009 | Guion-Johnson |

(Continued)

*Primary Examiner* — Daniel L Cerioni
*Assistant Examiner* — Raymond P Dulman
(74) *Attorney, Agent, or Firm* — Vincent G. LoTempio

(57) ABSTRACT

A wireless stethoscope provides a method of listening, recording and diagnosis of heart, lung, abdominal, vascular and other visceral organs sounds in place of a standard stethoscope. Simultaneous transfer of data occurs from the wireless stethoscope to an earpiece and a computing device, or an electronic medical records system, for recording, transmitting and analyzing information obtained from physical examination to provide a provisional diagnosis. A digital membrane portion has the capability to transmit sounds and subtle vibrations. The device measures acoustic transmissions that may include airborne transmission, impact transmission and flanking transmission. The device is capable of transmitting sound directly through an earbud port or to provide analog data for digital conversion and transmission of digital information. Further, the device includes sound wave control and noise reduction. The device can be switched from a bell to a membrane mode.

22 Claims, 10 Drawing Sheets

(51) Int. Cl.
   *H04R 1/10*     (2006.01)
   *H04R 7/04*     (2006.01)
   *A61B 5/318*    (2021.01)

(56) References Cited

U.S. PATENT DOCUMENTS

| | | |
|---|---|---|
| 8,200,277 B2 | 6/2012 | Lee |
| 8,447,043 B1 * | 5/2013 | Abbruscato ............. A61B 7/04 |
| | | 381/67 |
| 8,956,305 B2 | 2/2015 | Trice |
| 9,301,032 B1 | 3/2016 | Bello |
| 2008/0013747 A1 * | 1/2008 | Tran ........................ A61B 7/04 |
| | | 381/67 |
| 2008/0219464 A1 * | 9/2008 | Smith .................... G10K 15/02 |
| | | 381/67 |
| 2008/0232605 A1 * | 9/2008 | Bagha ...................... A61B 7/04 |
| | | 381/67 |
| 2014/0228927 A1 * | 8/2014 | Ahmad ................ A61H 39/002 |
| | | 607/148 |
| 2014/0270218 A1 | 9/2014 | Wang |
| 2014/0364755 A1 * | 12/2014 | Sankai ................... A61B 5/332 |
| | | 600/513 |
| 2016/0296200 A1 * | 10/2016 | Hinojosa ................ A61B 7/003 |
| 2016/0306940 A1 * | 10/2016 | Farhoud .................. H04W 4/80 |
| 2016/0338590 A1 * | 11/2016 | Sagalovich .......... A61B 5/0013 |
| 2017/0251231 A1 * | 8/2017 | Fullerton ........... H04N 21/8547 |
| 2018/0085062 A1 * | 3/2018 | Lee ..................... A61B 5/7278 |

* cited by examiner

WIRELESS STETHOSCOPE FOR TRANSMITTING, RECORDING, STORING AND DIAGNOSTIC CAPABILITIES INCLUDING AN EARPIECE

CROSS-REFERENCE TO RELATED APPLICATIONS

This application claims the priority benefit of U.S. Provisional Application Ser. No. 62/581,392, filed Nov. 3, 2017, the full disclosures of which are incorporated herein by reference.

BACKGROUND

Stethoscopes are used for auscultation, which is the process of listening to the internal sounds of the human body. Throughout medical history, the human body functional sounds were listened and described in words by physicians and other health care provided but the sound itself was never recorded. Wireless stethoscopes have been developed to utilize recording of medical information on mobile devices, personal computer and electronic medical records. These devices include many functions, including wireless communications capability, along with the ability to record, store, transmitting securely and analyze medical data.

Devices that allow physicians or patients to perform a physical examination not only used as a conventional stethoscope, but also record physiological data and transmit the data to their physician's computer or portable electronic device are known. These devices are particularly advantageous because they allow physicians to monitor their patients remotely. Physicians typically perform auscultation using a stethoscope to listen to the body's internal organ sounds that include but not limited to heart, lung, abdominal, and vascular systems. The device of the present disclosure allows these sounds to be recorded, transmitted and analyzed through Bluetooth or other wireless technology linked to a computer or smart phone apps.

The drawbacks associated with many of the existing wireless stethoscope devices include the inability to provide consistent feedback to allow a portable computing device to record, and analyze data accurately. As a result, consumers often are unable to use those devices therefore such devices have limited market value, and also prone to causing recording or transmitting inaccurate information that may lead to obtained useless information or misdiagnosis.

This application of Bluetooth or wireless stethoscopes can provide healthcare personnel with greater access to patient medical information beyond physical limitation such as being in the same room within less than 2 feet. Translation of auscultation to electrical signals enables amplification, filtering, and other signal processing to improve the diagnostic quality of audio signals presented to a clinician. Digitization of electronic data from a bluetooth stethoscope can improve efficiency and effectiveness of data recording, storage, transmission enable of sharing between patients and healthcare providers as well as among different healthcare providers and ultimately provided accurate and consistent medical information otherwise described in words by different personnel. This real time audio information has never before been recorded or stored. Examples of this application include incorporation of recorded body sounds into patient electronic medical records and replay of body sounds for transmission, download and analysis by one or more clinicians. Moreover, when digital audio files are transmitted over electronic data networks additional benefits may be realized. Such benefits include a review of data from patients at a distance and collaboration by healthcare personnel located in geographically different areas.

SUMMARY

The wireless stethoscope of the present disclosure provides a convenient solution to the problem of carrying a bulky stethoscope around the neck, in addition to allowing the physician to maintain physical distance between sick patients who may communicate disease but not decrease the bedside quality physical examination.

According to one embodiment of the present disclosure, a wireless electronic stethoscope device includes a main body, which may in one embodiment be generally of diamond shape, having four curved sides and four rounded points with beveled edges, wherein the top surface is curved and has a greater surface area than the bottom surface which contains a sensing portion; electronic pressure and vibration sensors for data collection; a circuit board to communicate information and receive operational commands; a wireless communication module to transmit and receive data; and a power module including a rechargeable low energy lithium battery.

In the present disclosure, the transfer of data from the wireless stethoscope not only maintains the traditional acoustic sound through a well-designed electronic earpiece that can be amplified, but also through various wireless technologies to communicate to a computer or mobile phone, as well as instruments compatible with software for storing, transmitting, and analyzing the data, to allow physicians to monitor their patient remotely or sharing real time physical examination sounds and conforming specific diagnosis between physicians of different specialties.

A problem with existing wireless stethoscope devices is that the data produced is not reproducible or is inconsistent. To solve this problem, the present disclosure combines an earpiece within the system that can confirm the best physical location of heart sounds or lung sounds or other sounds before the data is recorded or transmitted through a recording/analytical device, such as but not limited a computer, a tablet or a smartphone. The earpiece allows a user get instant feedback in order to identify a location on the body where a clear heartbeat or breathing or other visceral organ system sound is detectable, or in where traditional stethoscope has been used for physical examination. The wireless connection from and to the devices may include but is not limited to wiMax, wifi, blue tooth, ZigBee, microwave, infrared and femtocell, metrocell and picocell. The system of the present disclosure utilizes digital sound detection and transmission; a digital diaphragm or membrane with a sound detection, vibration detection and a pressure sensor incorporated with detection of misuse digital sound sampling technology. A beveled edge of the stethoscope design allows for easy grasping the device without additional mechanisms.

A critical component of the device of the present disclosure is the digital membrane (diaphragm) portion that not only can amplify sounds acquired from patient, but is also capable of transmitting subtle vibration when gentle pressure was applied to the body. In one embodiment, the device of the present disclosure measures acoustic transmissions including airborne transmission, impact transmission and flanking transmission. The digital membrane may utilize greater pressure and vibration transmission signals, when compared to sound amplification signals. In one preferred embodiment, greater than 90% of pressure and vibration transmission signals are utilized, when compared to sound transmission signals.

A second aspect of the device of the present disclosure is that the design allows for sound wave control and noise reduction. With a touch of a button the device is able to change measured frequency from 100-2000 Hz of membrane measurement to a stethoscope bell measurement (20-500 Hz). Further, the device may utilize a low energy rechargeable battery capable of increasing battery life. The device may include a short-range blue tooth or other wireless transmission mode to ensure the security of data transmission to or from smart handheld devices or a PC for electronic medical records.

An ear piece may be a physical plug in the form of ear buds, and may utilize digital wireless connection of ear pieces including but not limited to WiMAX, Wi-Fi, Bluetooth, ZigBee, microwave, infrared and femtocell. Instructions provided to the user on where to initially place the stethoscope on a patient's chest may be included in the system of the present disclosure.

The device of the present disclosure is intended to replace standard manual stethoscope with digital and Bluetooth technology and be used as a remote tool for telemedicine. Further, the device may be used for remote data recording, with storage in and transmission to and from an electronical medical system. In one embodiment, the device may also be be used as diagnostic screen tool for physical examination. In an embodiment, the device is capable of recording, transmitting body organ sounds and includes basic diagnostic capacity through accurate data transfer with a computing device such as, but not limited to, a smart phone, tablet or lap top computer or desk top personal computer, by using computer software capability of analyzing transformed data. The device according to the present disclosure is capable of operating as an external cardiac rhythm monitor, having functions that include continuous heart monitoring over a period of time, and also may function as an event monitor for detecting heart arrhythmic disorders.

The device may include a motherboard (internal circuit board) and software for display on a smart phone or a computer by using a direct cable connection or wireless connection. The device may be capable of performing as otoscope by attachment with a digital camera and electrocardiograms (ECG), obtaining ultrasound imagines including but not limited to M mode, Doppler study, and 2D and 3D ultrasound images with a specific attachment. The information provided by the device of the present disclosure is not limited to cardiac images but also may include other visceral organs where a stethoscope may be used, including lung, abdominal and vascular studies.

It is a first object of the present disclosure to describe a system and method for a wireless stethoscope having an earpiece directly or wirelessly connected to the digital stethoscope, and the stethoscope to a computer device with recording, storage and transmitting analysis functions.

It is a further object of the present disclosure to describe a system and method for a wireless stethoscope having the capacity to change measurement from membrane transmission (100-2000 Hz) to bell sound (20-500 Hz) transmission with a switch.

It is a further object of the present disclosure to describe a system and method for a wireless stethoscope to record and transmit sounds not only by sound amplification but also capable of detecting and transmitting subtle vibration and pressure sensed information.

It is a further object of the present disclosure to describe a system and method for a wireless stethoscope having a built-in electronic pressure and vibration sensors that meets ISO 9001 and IEC 60601 standards.

It is a further object of the present disclosure to describe a system and method a system and method for a wireless stethoscope that has capacity to detect heart rhythm disorder by measuring and analyzing electric waveforms.

It is a further object of the present disclosure to describe a system and method for a wireless stethoscope that has capacity to adapt a twelve leads electrocardiography (ECG) probe or ultrasound probe to record and analyze twelve leads ECG and Doppler images, M waves, and 2D and 3D images, respectively.

It is a further object of the present disclosure to describe a wireless stethoscope that is capable of monitoring cardiac rhythm from continuous recording including, but not limited to, 24-hour recording, and also function as an event monitor recording device.

It is a further object of the present disclosure to describe a wireless stethoscope that is tubing free, adaptable to wire/wireless ear buds and capable of transmitting organ sounds wirelessly, and performs these tasks in addition to tasks performed by conventional stethoscopes.

BRIEF DESCRIPTION OF THE DRAWINGS

Preferred embodiments of the present invention will now be described, by way of example only, with reference to the attached Figures, wherein.

DETAILED DESCRIPTION

Figure 1:
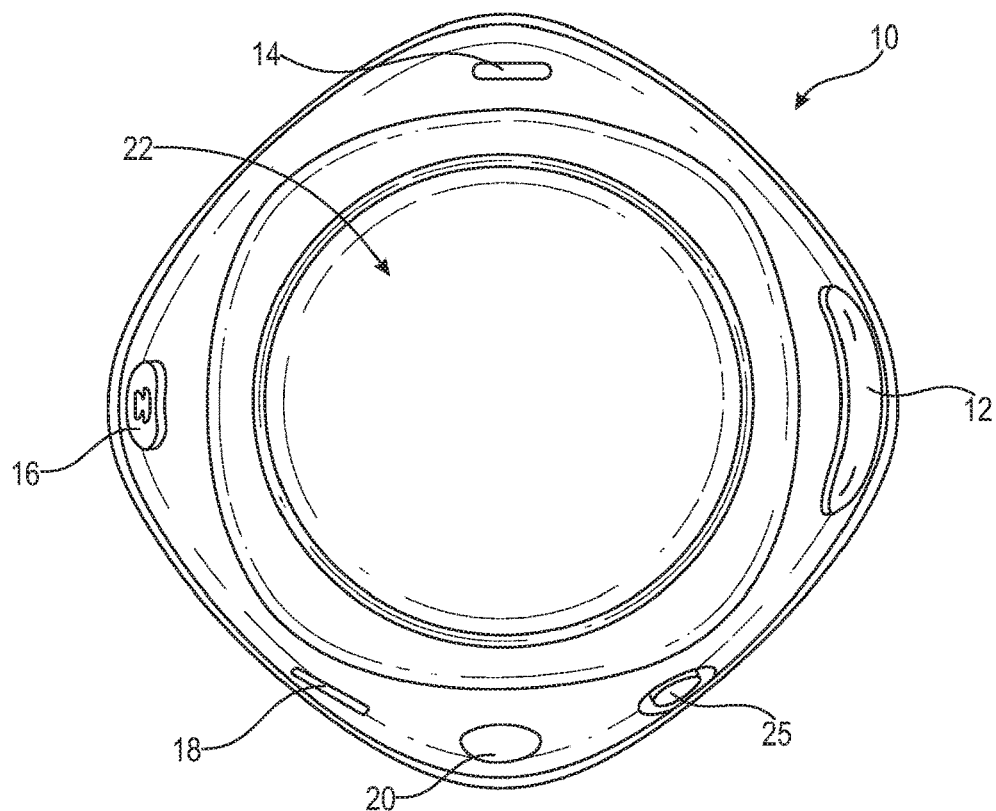
FIG. 1 shows a bottom view of the wireless stethoscope of the present disclosure.

In the following detailed description, for purposes of explanation, numerous specific details are set forth in order to attain a thorough understanding of the disclosed embodiments. It will be apparent, however, that one or more embodiments may be practiced without these specific details. In other instances, well-known structures and devices are schematically shown in order to simplify the drawing.

As used in the description herein and throughout the claims that follow, the meaning of "a", "an", and "the" includes reference to the plural unless the context clearly dictates otherwise. Also, as used in the description herein and throughout the claims that follow, the terms "comprise or comprising", "include or including", "have or having", "contain or containing" and the like are to be understood to be open-ended, ie., to mean including but not limited to. As used in the description herein and throughout the claims that follow, the meaning of "in" includes "in" and "on" unless the context clearly dictates otherwise.

The wireless stethoscope of the present disclosure provides a convenient solution to the problem of carrying a bulky stethoscope around the neck, in addition to allowing the physician to maintain distance between sick patients who may communicate disease. In the present disclosure, the transfer of data from the wireless stethoscope to an earpiece and mobile devices including but not limited to smart phone, tablet, PC and instruments compatible with software for recording, transmitting and analyzing the data, allows the physician to decrease the chance of misdiagnosis.

The present disclosure relates to a wireless electronic stethoscope. The description discloses physical structure, functional component modules, processes of operation, and methods of use of the wireless electronic stethoscope.

The wireless stethoscope (stethoscope) is designed to have a physical structure and an arrangement of user interface controls that together allow for ease of operation by a patient or clinician. As shown in FIG. 1, a bottom view of wireless stethoscope 10 of one embodiment of the present disclosure has a volume control switch 12. Wireless stethoscope 10 has a digital membrane (diaphragm) 22 having vibration, pressure and audio sensing capacity. A device attachment port 14 for directly connecting to Wi-Fi or internet is adjacent digital membrane 22. Wireless stethoscope 10 may include a pressure sensor, vibration sensor and digital sound amplification. Wireless stethoscope 10 has a membrane and bell switch 16, which allows for switching between the bell and membrane type of tests. In a traditional stethoscope, the membrane, or diaphragm, is best for higher pitched sounds, like breath sounds and normal heart sounds. The bell is best for detecting lower pitch sounds, like some heart murmurs, and some bowel sounds. The present disclosure includes a digital version of the traditional membrane and bell uses of a stethoscope. Universal charge port 18, can be used for charging a battery 72 (shown in FIG. 6) and may be adjacent ear phone plug 20 or a blue tooth ear phone. Wireless stethoscope 10 also includes on/off switch 25 which is also capable of resetting the device.

Figure 2:
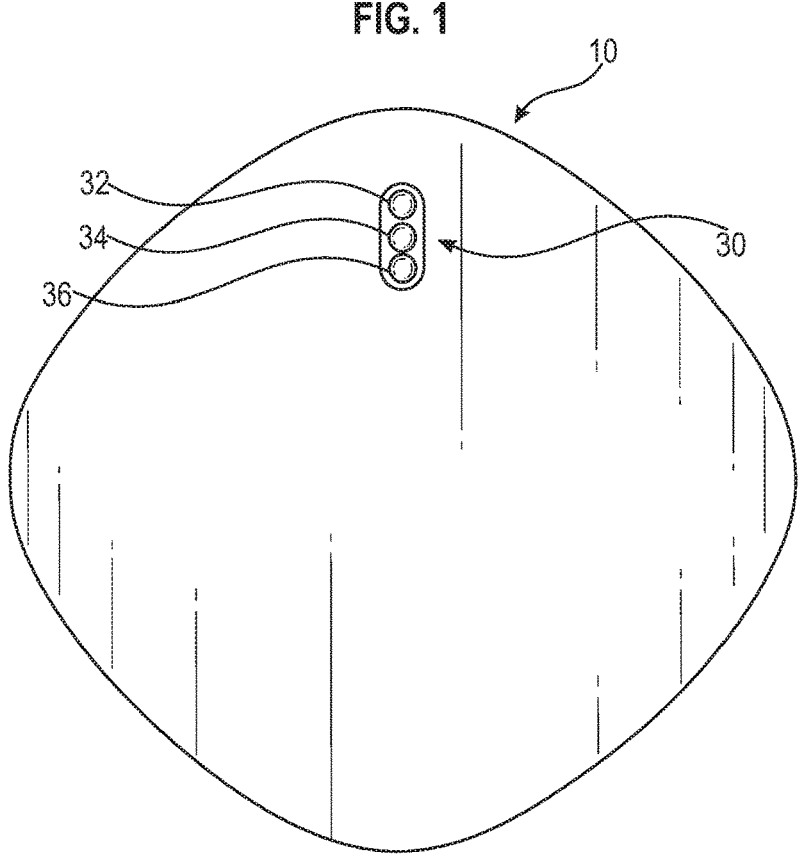
FIG. 2 shows a top view of the wireless stethoscope of the present disclosure.

As shown in FIG. 2, a top view of wireless includes LED indicator panel 30. LED indicator panel 30 may include a power indicator 32, a Bluetooth indicator 34, and a mode indicator 36, which displays whether the wireless stethoscope 10 is in bell mode or membrane mode.

Figure 3:
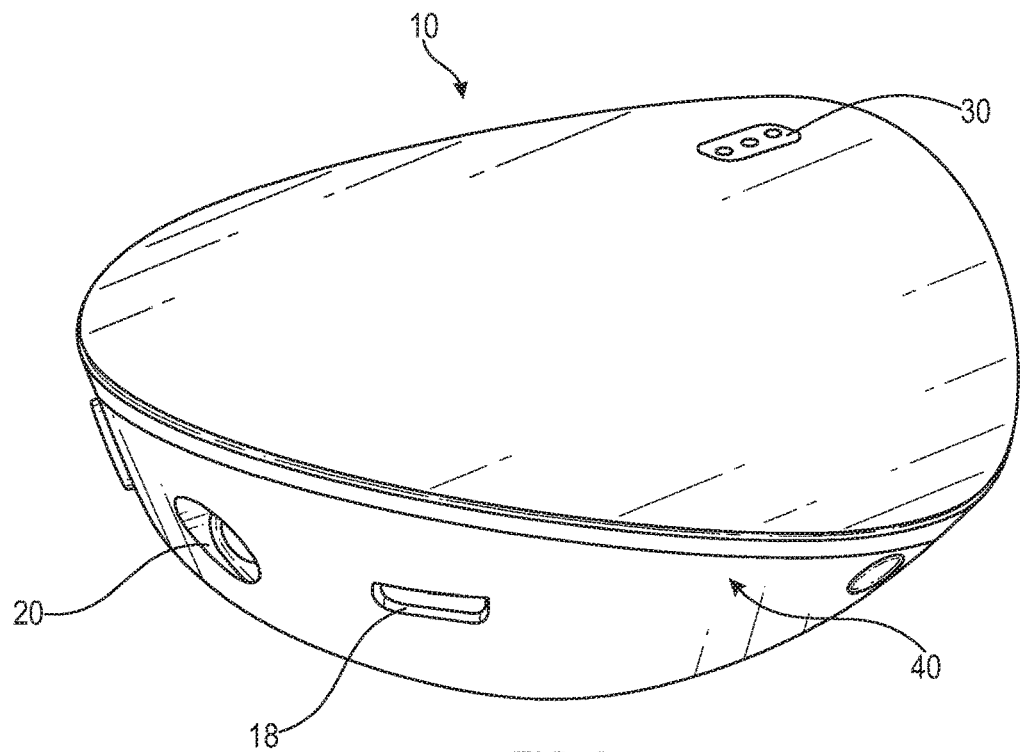
FIG. 3 shows a side perspective view of the wireless stethoscope of the present disclosure.

With regard to FIG. 3, in one embodiment, wireless stethoscope 10 may have a beveled edge 40. In certain embodiments, beveled edge 40 may have an approximate angle of between 60 and 75 degrees from a bottom surface of wireless stethoscope 10. Beveled edge 40 allows for easier gripping and use of the adjustable features of wireless stethoscope 10. In one embodiment, wireless stethoscope 10 has a curved upper surface to facilitate gripping. The curvature occurs from a first side to a second side, as opposed to from front to back. At the peak of the curved surface may be LED indicator panel 30.

Figure 4:
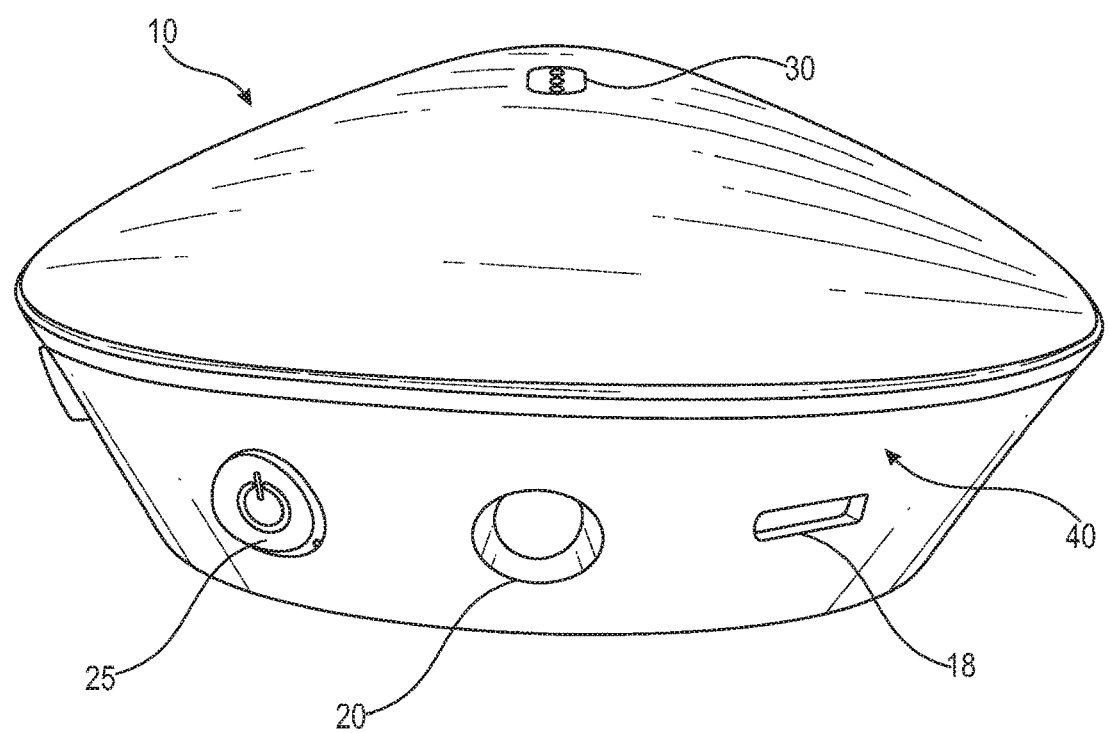
FIG. 4 shows a front view of the wireless stethoscope of the present disclosure.

With regard to FIG. 4, in one embodiment, wireless stethoscope 10 includes an ear bud jack 20, an on/off switch 25 and a USB charge port 18 at a back portion of wireless stethoscope 10. Ear bud jack 20 may be symmetrically placed at the back point, one of the four points on the diamond shape of wireless stethoscope 10, on the rear portion of beveled edge 40 of wireless stethoscope 10.

Figure 5:
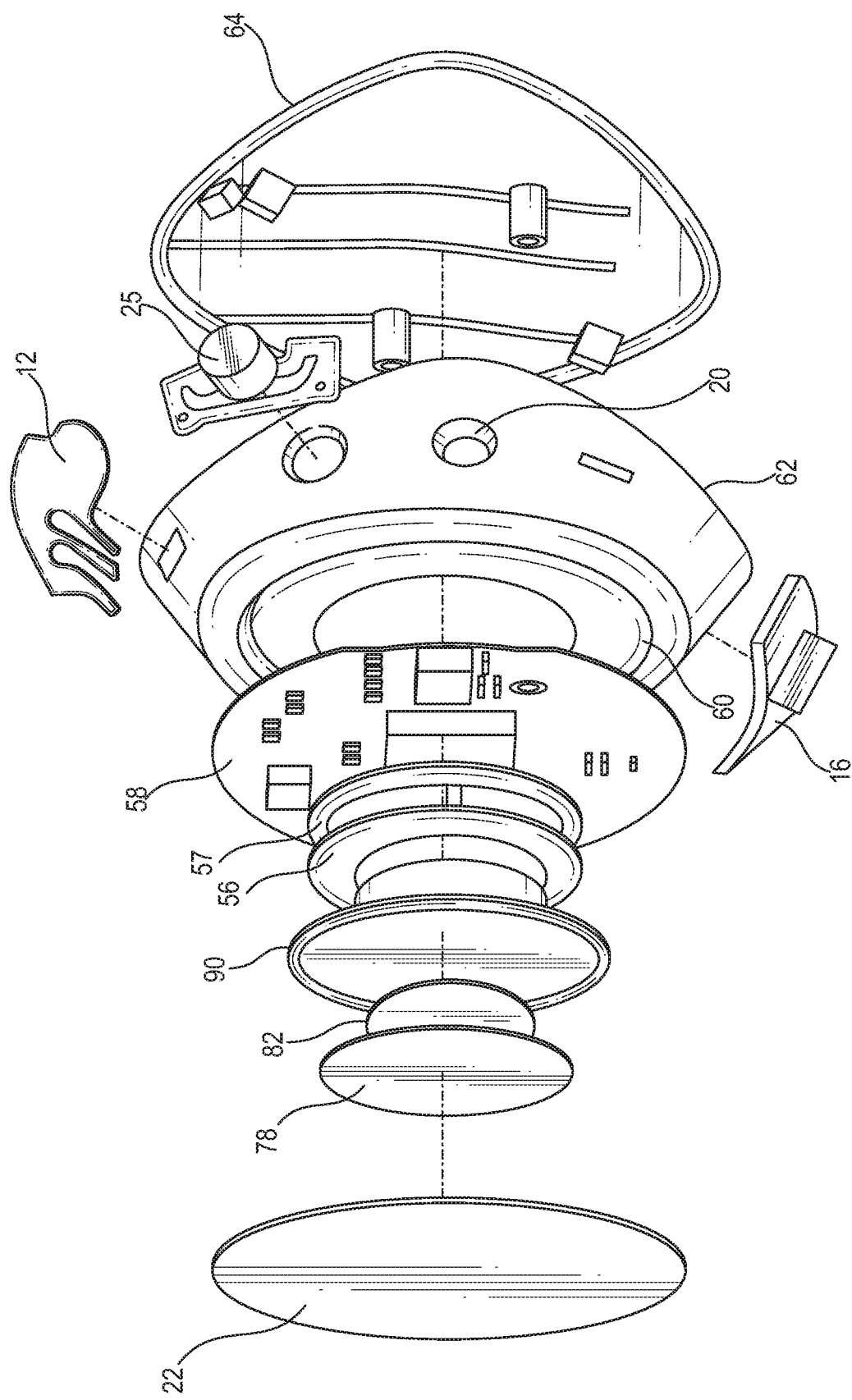
FIG. 5 shows an exploded view of the wireless stethoscope of the present disclosure.
Figure 8:
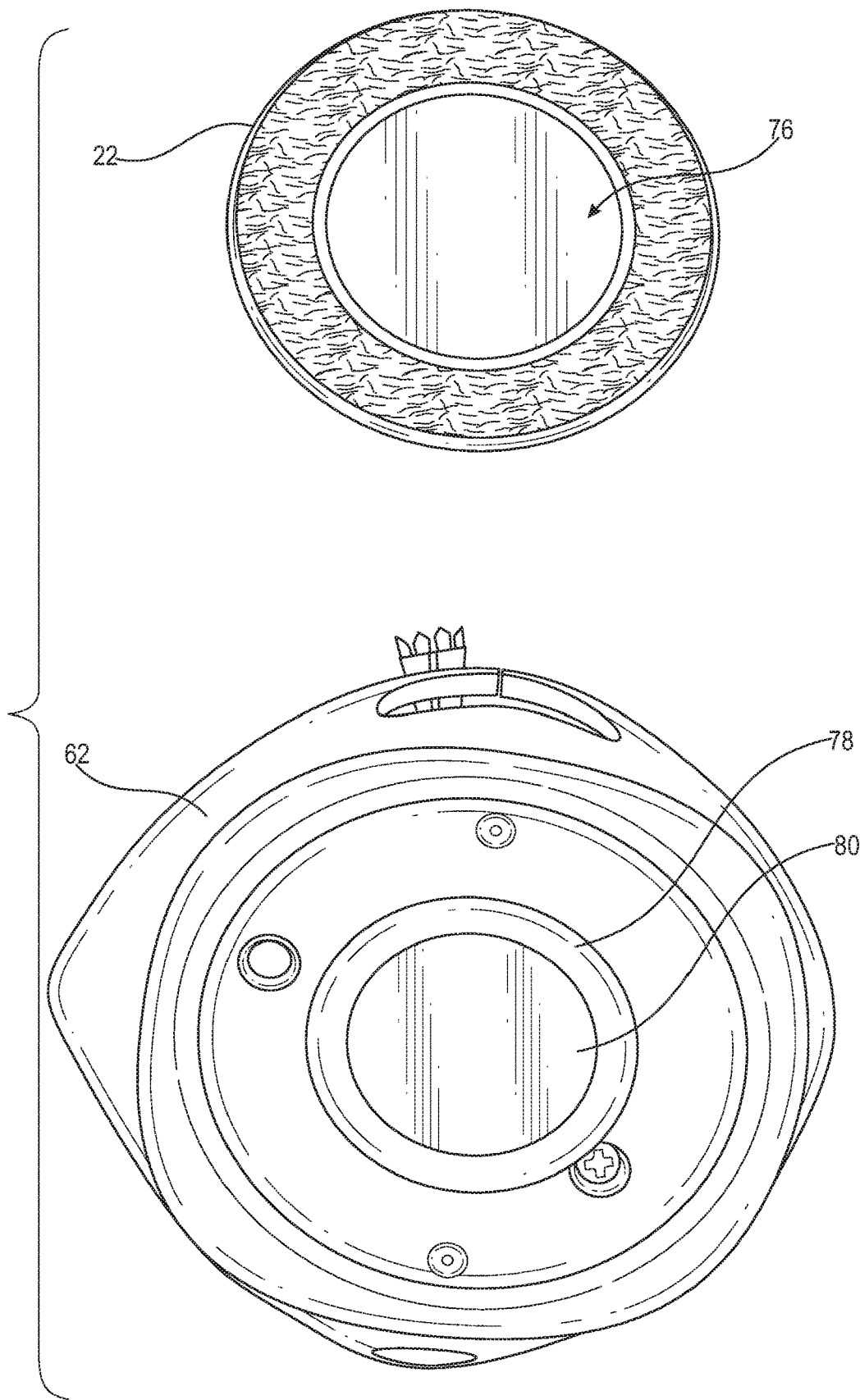
FIG. 8 shows a top view of a portion of the sensor system where the membrane has been removed from the wireless stethoscope of the present disclosure.

With regard to FIG. 5, an exploded view of the wireless stethoscope of the present disclosure shows sensor membrane 22, which comprises an external portion of the sensor system. Membrane 22 may be comprised of synthetic silicones and rubber material that are capable of sensing vibration and pressure. In a first embodiment, the diameter of membrane 22 is 42 mm. In the first embodiment, the thickness of membrane 22 is 1 mm in the area surrounding membrane recess 76. Membrane 22 has, on a back portion, a membrane recess 76, as shown in FIG. 8. In the first embodiment a diameter of membrane recess 76 is 25 mm and a thickness of membrane 22 in the area of the recess is 0.4 mm. Membrane 22 fits in to a circular groove in main housing unit 62 and, when wireless stethoscope 10 is assembled, an outer surface of membrane 22 is flush with the outer edge on the bottom of main housing unit 62.

Figure 9:
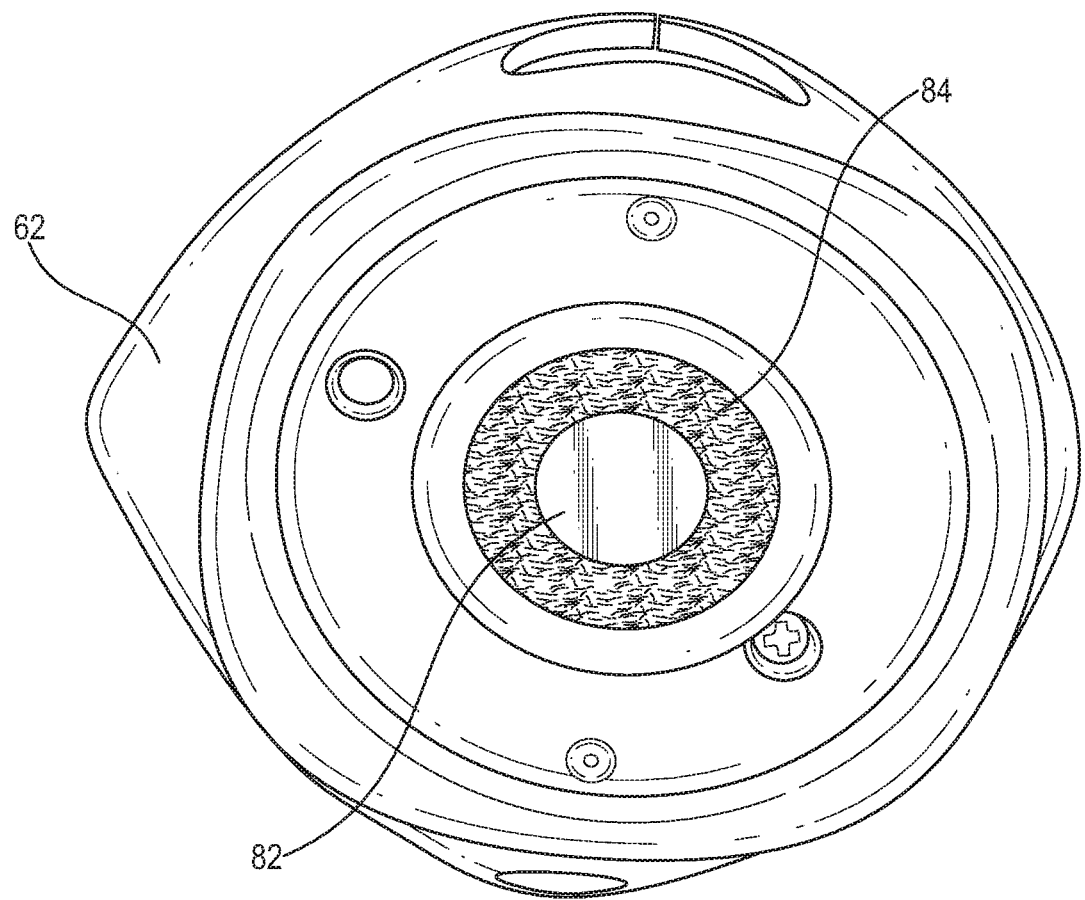
FIG. 9 shows a top view of the wireless stethoscope of the present disclosure where the plastic cover over the sensor has been removed.
Figure 10:
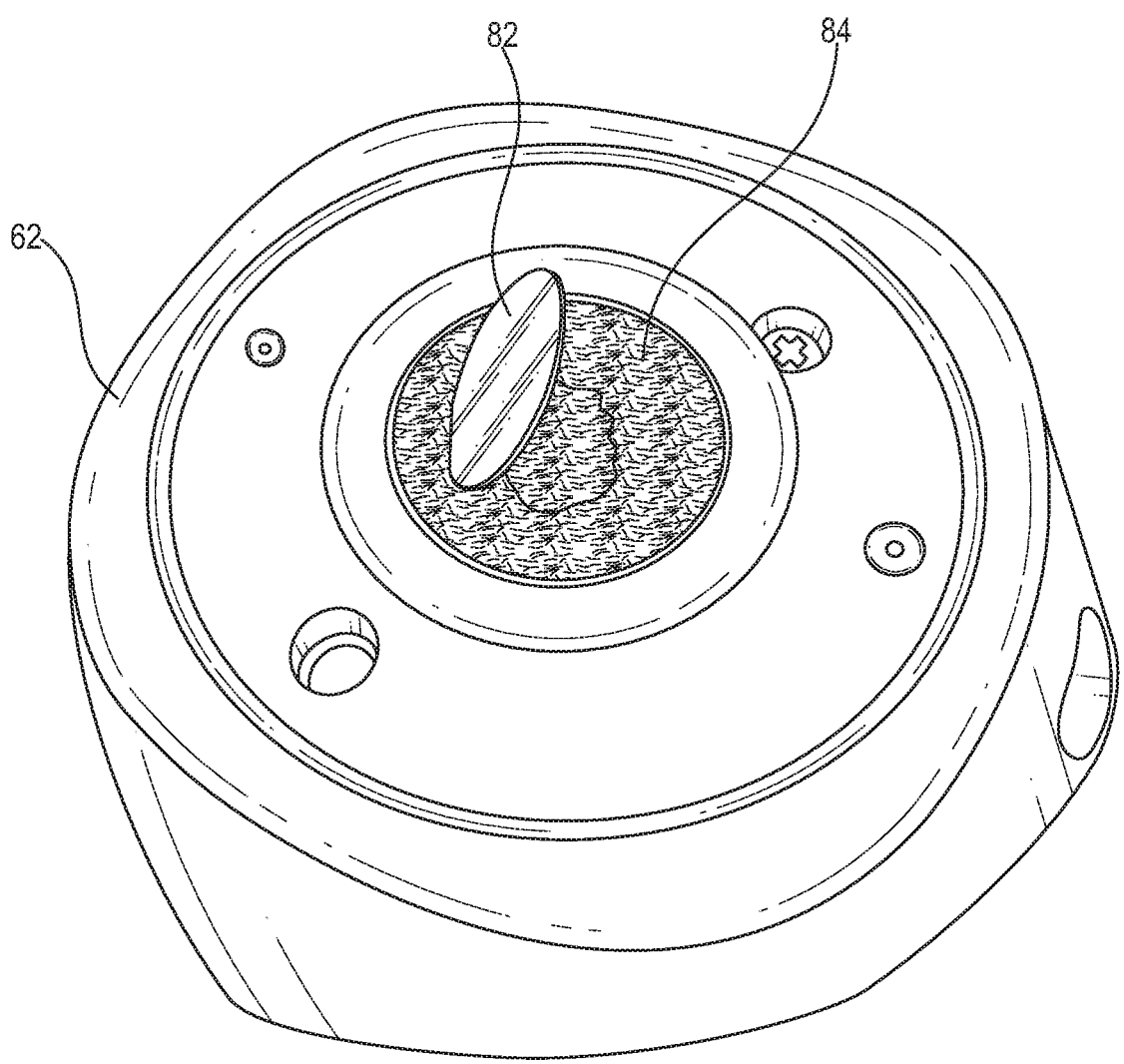
FIG. 10 shows a perspective view of the wireless stethoscope of the present disclosure with a portion of the first plate separated from the plate isolation portion.
Figure 11:
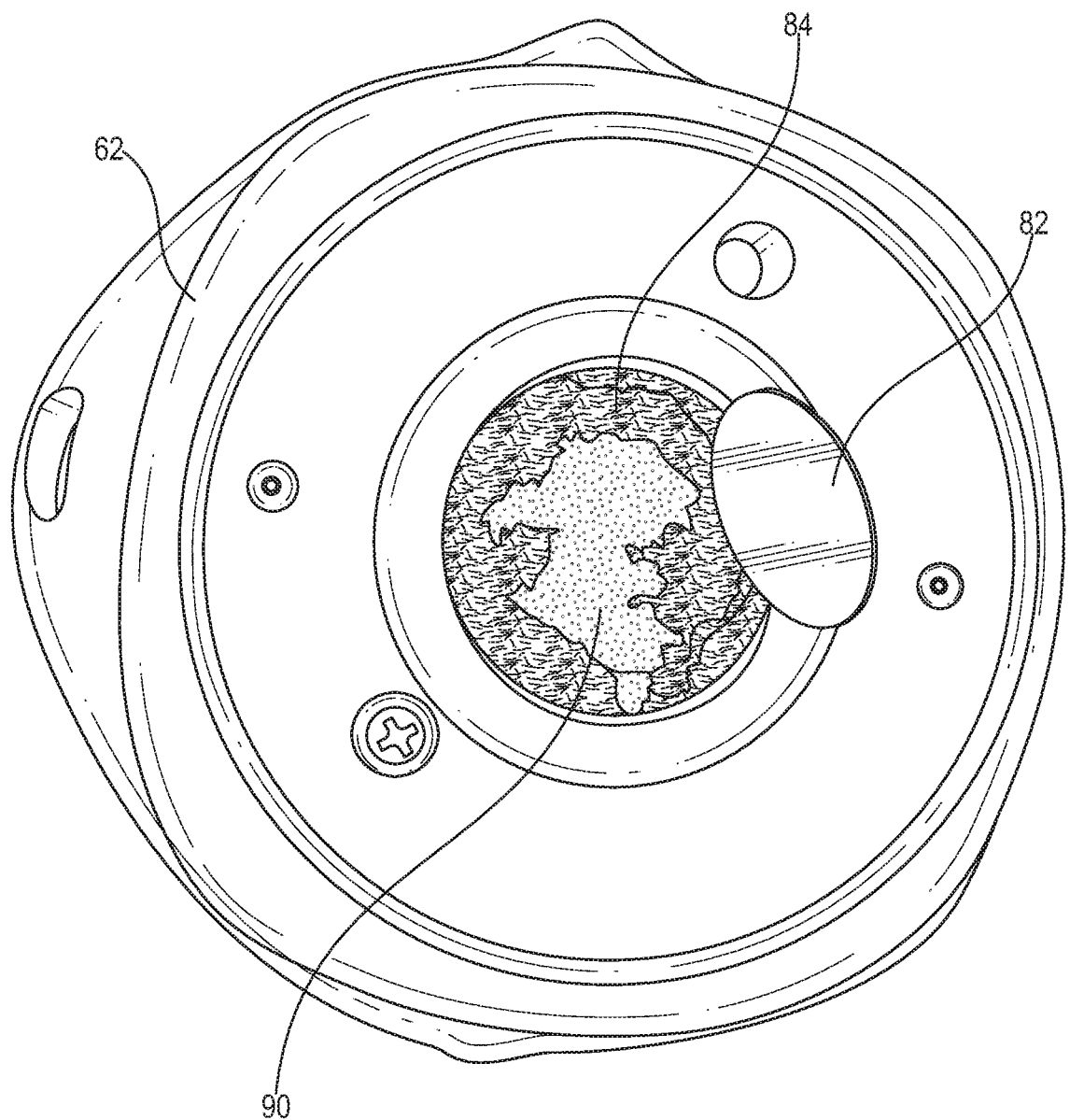
FIG. 11 shows a top view of the wireless stethoscope of the present disclosure where a portion of the sensor is exposed.

Membrane 22 is in contact with ring isolation layer 78. Isolation tape 52 includes a ring isolation layer 78 which may have dimensions of 3 mm in width and 18 mm in diameter, (shown in FIG. 8) covering a plastic recess plate 80 with an opening of 4 mm×12 mm (shown in FIG. 8). Underneath ring isolation layer 78 is first plate 82, as shown in FIGS. 9 and 10, which may be comprised of stainless steel and has in a first embodiment a diameter of 12 mm and a thickness of 0.5 mm. First plate 82 functions in measuring higher frequencies which correspond to the membrane function of wireless stethoscope 10, where first plate 82 functions in combination with second plate 90, which may be comprised of copper, when the second plate 90 is not electrically activated. Second plate 90 has in a first embodiment a diameter of 15 mm and a thickness of 0.3 mm. First plate 82 and second plate 90 are part of the sensor system of wireless stethoscope 10, and therefore may be considered sensor system plates. The stethoscope membrane function, as described above, corresponds to membrane measurement of a frequency of approximately 100-2000 Hz, whereas a stethoscope bell measurement occurs at approximately 20-500 Hz. The bell function of the present disclosure refers to a digital capability approximately equivalent to that of a "bell" feature of a traditional stethoscope.

Between first plate 82 and second plate 90 is plate isolation portion 84, which is shown in FIGS. 9 and 10 (not shown in FIG. 5). Plate isolation portion 84 serves to provide a barrier between second plate 90 and first plate 82. The combination of second plate 90, which may be comprised of copper, and first plate 82 allows for a membrane function measurement when the first plate 82 is not electronically activated.

Second plate 90 is conductive and may preferably be comprised of copper. Second plate 90 is attached to circuit board 58 through an electrode. When second plate 90 is electronically activated by switching from membrane mode to bell mode with the membrane and bell switch 16, measurements are made in the lower frequency range at approximately 20-500 Hz. Plate isolation portion 84 may comprised of rubber with acrylic resin. Plate isolation portion 84 is, in a first embodiment, 0.2 mm in thickness.

Second plate 90 is connected to specific electrode for controlling and transmitting sounds by a gradually layered physical mechanism and electrical control. First plate 82 is 12 mm in diameter that is exactly 3 mm smaller than second plate 90, which is 15 mm. Both first plate 82 and second plate 90 can act as one unit or electronically separated as it sits on top of rubber/silicon ring insulation layer 78 which is, in one embodiment, 3 mm in width and 18 mm in diameter. Ring insulation layer 78 may, in one embodiment, be about 0.5 mm in height and therefore create a space with an opening.

Isolation ring 56 is, in a first embodiment, has a center hollow space 12 mm diameter and isolation ring 56 has a diameter of 18 mm and a thickness of 0.5 mm, where the ring width is 3 mm. Isolation ring 56 is made of rubber or silicone material and has an electrode embedded within. Plastic center piece 57, having is 18 mm in diameter with a center rectangular opening measured at 3 mm by 18 mm and is disposed between circuit board 58 and isolation ring 56. An air gap exists between second plate 90 and any plastic component of main housing unit 62. Therefore, a bottom side of second plate 90 is adhered to plate isolation portion 84, and on a top side of second plate 90 is adhered an electrode connected to circuit board 58. The air gap exists on the top side of second plate 90. The electrode passes through a slit in main housing unit 62 that separates circuit board 58 from Second isolation unit 60 is disposed between circuit board 58 and main housing unit 62. Upper case cover 64 encloses the internal components of wireless stethoscope 10. Volume button 12 allows for adjustment of the volume for user listening. Power button 25 allows a user to turn wireless stethoscope 10 on and off, as well as reset wireless stethoscope 10.

Figure 6:
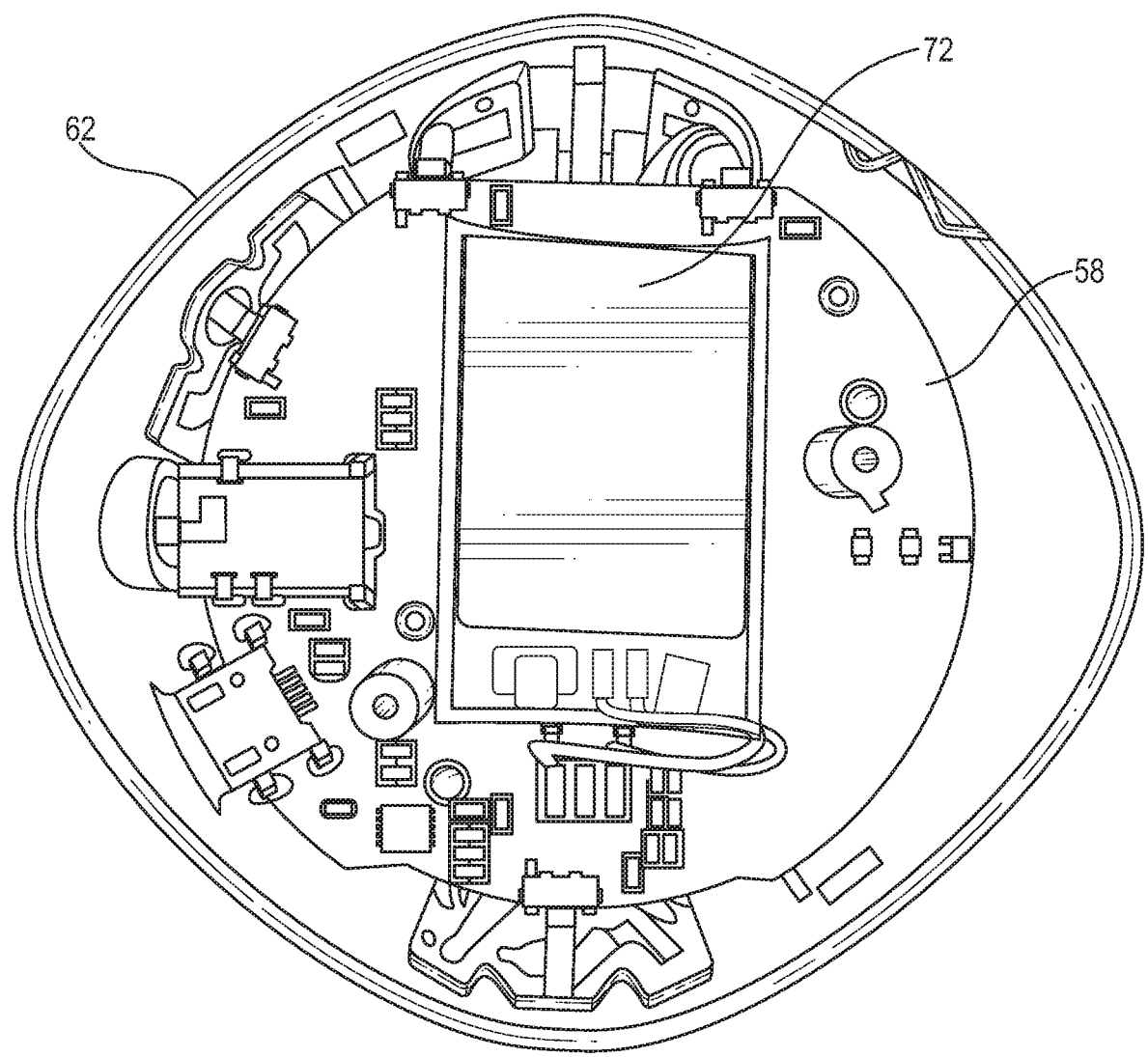
FIG. 6 shows a top view of the circuit board of the wireless stethoscope of the present disclosure.

With regard to FIG. 6, a top view is shown with upper case cover 64 removed. Battery 72 is shown attached to circuit board 58. These components are shown housed in main housing unit 62.

Figure 7:
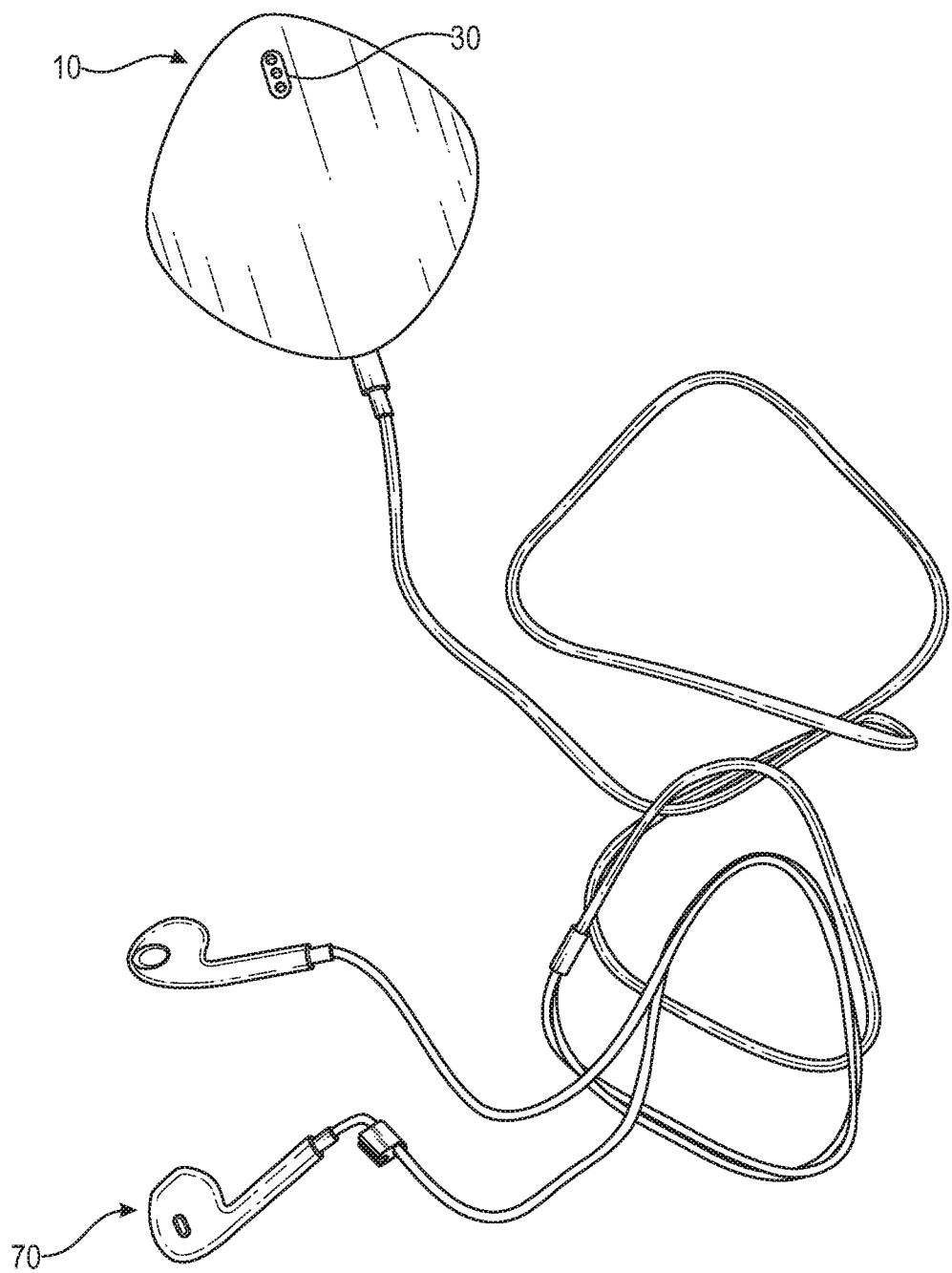
FIG. 7 shows earbuds attached to the wireless stethoscope of the present disclosure.

With regard to FIG. 7, a top view of wireless stethoscope 10 connected to earbuds 70. Earbuds 70 allow a user to locate a heartbeat, breathing sounds and other body organ sounds acquired with wireless stethoscope 10 in conjunction with a wired or wireless earbuds or other listening devices. Once audio from heart, lung or other organ sounds is identified located, a program in a portable computing device such as a smartphone recognizes proper feedback and begins the recording and analyzing process.

An important component of the present disclosure is the ability of the system to create reproducible and consistent data that is capable of being transmitted through Bluetooth or other wireless technology means. Therefore, a number of components are combined and used simultaneously to allow a health care professional or other user to locate a heartbeat, breathing sounds and other body organ sounds through wireless stethoscope 10.

Figure 12:
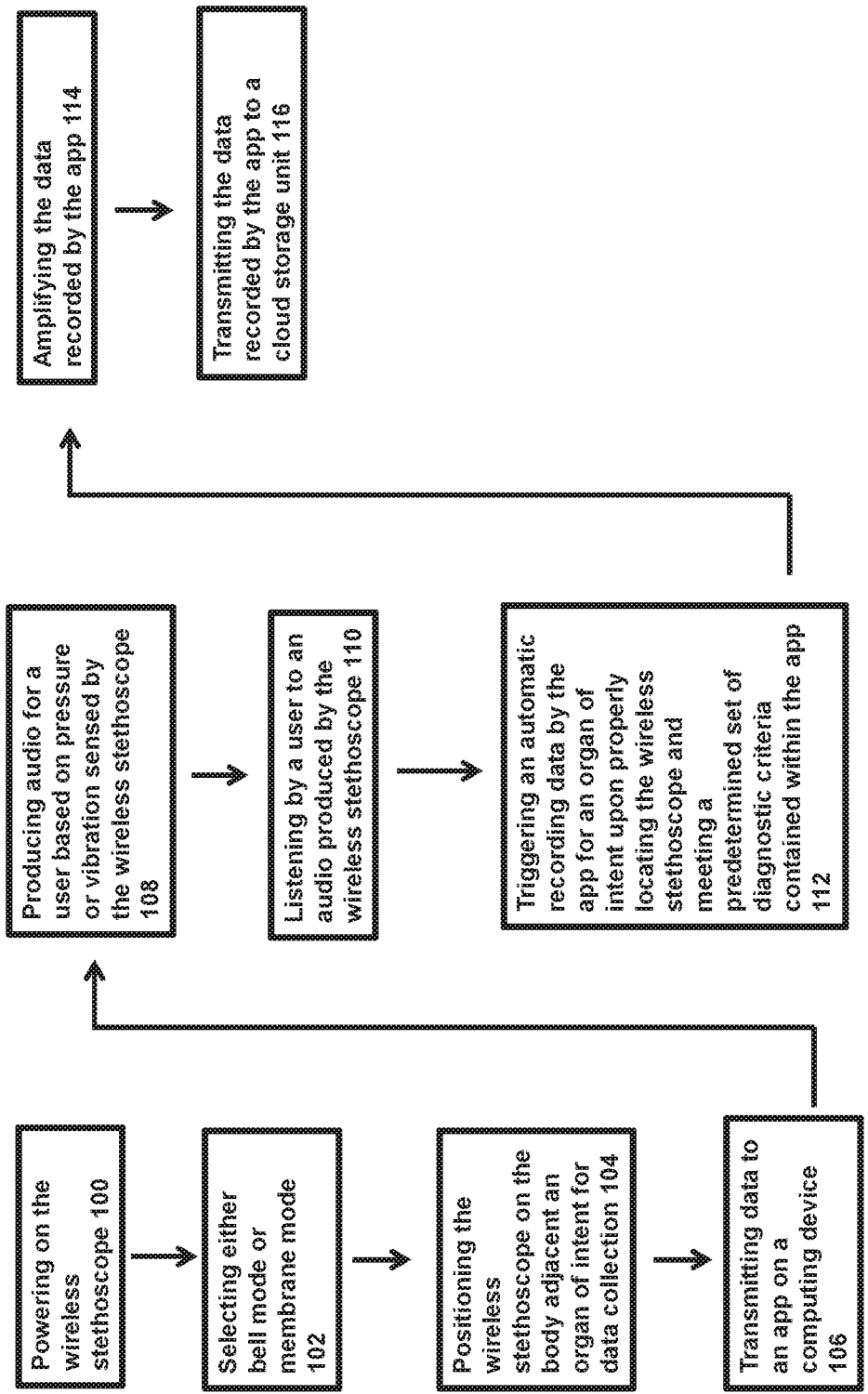
FIG. 12 shows a flow chart according to the present disclosure.

With regard to FIG. 12, a flow chart shows the steps of powering on the wireless stethoscope 100, selecting either bell mode or membrane mode 102, positioning the wireless stethoscope on the body adjacent an organ of intent for data collection 104, transmitting data to an app on a computing device 106, producing audio for a user based on pressure or vibration sensed by the wireless stethoscope 108, listening by a user to an audio produced by the wireless stethoscope 110, triggering an automatic recording data by the app for an organ of intent upon properly locating the wireless stethoscope and meeting a predetermined set of diagnostic criteria contained within the app 112, amplifying the data recorded by the app 114, and transmitting the data recorded by the app to a cloud storage unit 116.

The detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper," "lower," "left," "rear," "right," "front," "vertical," "horizontal," and derivatives thereof shall relate to the invention as oriented in FIG. 1. Furthermore, there is no intention to be bound by any expressed or implied theory presented in the preceding technical field, background, brief summary or the following detailed description. It is also to be understood that the specific systems and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

At the outset, it should be clearly understood that like reference numerals are intended to identify the same structural elements, portions, or surfaces consistently throughout the several drawing figures, as may be further described or explained by the entire written specification of which this detailed description is an integral part. The drawings are intended to be read together with the specification and are to be construed as a portion of the entire "written description" of this invention as required by 35 U.S.C. § 112.

Since many modifications, variations, and changes in detail can be made to the described preferred embodiments of the invention, it is intended that all matters in the written description and shown in the accompanying drawings be interpreted as illustrative and not in a limiting sense. Thus, the scope of the invention should be determined by the appended claims and their legal equivalence.

Having described the presently preferred embodiments of the invention, it is to be understood that the invention may otherwise be embodied within the scope of the appended claims.

What is claimed is:

1. A wireless stethoscope, comprising:
   a membrane that includes a plurality of sensors configured to collect data;
   a circuit board;
   an electrode connected to the circuit board;
   a first plate;
   a second plate attached to the circuit board;
   a ring isolation layer between the membrane and the first plate;
   an isolation ring between the second plate and the circuit board, wherein
      the electrode is embedded within the isolation ring, and
      each of the isolation ring, the second plate, and the circuit board is along a same axis;
   a port on the wireless stethoscope, wherein the port is configured to connect an external earphone device;
   a switch button on the wireless stethoscope; and a battery attached to the circuit board, wherein the circuit board is configured to:
  determine that the wireless stethoscope is positioned adjacent to an organ of intent;
  switch between a bell mode and a membrane mode based on a user operation on the switch button; and
  record the data based on:
    the determination that the wireless stethoscope is positioned adjacent to an organ, and
    switch to one of the bell mode or the membrane mode.

2. The wireless stethoscope of claim 1, further comprising a plate isolation portion, wherein
the first plate is proximal to the membrane,
the second plate is distal to the membrane, and
the first plate and the second plate are separated by the plate isolation portion.

3. The wireless stethoscope of claim 1, wherein the first plate is comprised of steel and the second plate is comprised of copper.

4. The wireless stethoscope of claim 1, wherein the circuit board is further configured to:
collect, in the bell mode, the data between a frequency of 20-500 Hz, and
collect, in the membrane mode, the data between a frequency of 100-2000 Hz.

5. The wireless stethoscope of claim 1, further comprising an earpiece directly or wirelessly connected to the wireless stethoscope, wherein a computer device is connected to the wireless stethoscope for recording the data, storage of the data, transmitting the data and analysis on the data.

6. The wireless stethoscope of claim 1, wherein the wireless stethoscope is capable of recording the data and transmitting the data through sound amplification.

7. The wireless stethoscope of claim 1, wherein the wireless stethoscope has a built-in pressure sensor of the plurality of sensors and a vibration sensor of the plurality of sensors.

8. The wireless stethoscope of claim 1, wherein
the collected data includes heart sound waves, and
the wireless stethoscope is capable of acting as a rhythm monitor device through the heart sound waves.

9. The wireless stethoscope of claim 1, wherein
the collected data includes ultra sound data, and
the wireless stethoscope is capable of adapting and analyzing the ultrasound data via at least one of Doppler imaging, M waves, 2D, or 3D imaging.

10. The wireless stethoscope of claim 1, wherein
the wireless stethoscope is capable of monitoring a cardiac rhythm from continuous recording the data over an extended period of time,
the wireless stethoscope is capable of self-activation, and
the wireless stethoscope is capable of being triggered by arrhythmia and function as an event monitor.

11. The wireless stethoscope of claim 1, wherein
the wireless stethoscope is capable of performing electrocardiography in a separate bipolar lead, and
the collected data includes electrocardiography data and the electrocardiography data is resynthesized and analyzed using software capable of detecting a cardiac ischemic condition.

12. The wireless stethoscope of claim 1, wherein
the collected data includes audio data,
the collected data corresponds to audio data of each of a heart, a lung, and a vascular system, including both arterial and venous systems, and visceral organs,
the collected data is transmitted wirelessly to a computing device such as a smart phone, a tablet, and a personal computer, and
the collected data is directed to at least one of a cloud computing system or an electronic medical records system.

13. A wireless stethoscope system, comprising:
a wireless stethoscope having:
  a membrane that includes a plurality of sensors configured to collect data;
  a circuit board;
  an electrode connected to the circuit board;
  a first plate;
  a second plate attached to the circuit board;
  a ring isolation layer between the membrane and the first plate;
  an isolation ring between the second plate and the circuit board, wherein
    the electrode is embedded within the isolation ring, and
    each of the isolation ring, the second plate, and the circuit board is along a same axis;
  a switch button on the wireless stethoscope; and
  a battery attached to the circuit board, wherein the circuit board is configured to:
    determine that the wireless stethoscope is positioned adjacent to an organ of intent;
    switch between a bell mode and a membrane mode based on a user operation on the switch button; and
    record the data based on:
      the determination that the wireless stethoscope is positioned adjacent to an organ, and
      switched one of the bell mode or the membrane mode for storing energy.

14. The wireless stethoscope system of claim 13, wherein the wireless stethoscope has a beveled edge such that a top surface of the wireless stethoscope has a larger surface area than a bottom surface of the wireless stethoscope.

15. The wireless stethoscope system of claim 13, wherein
the wireless stethoscope has a port for connecting an audio component that provides a user with the collected data, and
the port is configured to connect to a set of earbuds.

16. The wireless stethoscope system of claim 13, wherein membrane has a surface area that is at least three times greater than a surface area of the second plate.

17. The wireless stethoscope system of claim 13, further comprising an LED indicator panel on a top surface of the wireless stethoscope, wherein
the LED indicator panel includes a power indicator, a Bluetooth indicator, and a model indicator,
the model indicator indicates one of the bell mode or the membrane mode.

18. The wireless stethoscope system of claim 13, wherein the wireless stethoscope is connected to a server that operates as a HIPPA compliant cloud storage unit.

19. The wireless stethoscope system of claim 13, wherein the wireless stethoscope is connected to a remote server for receiving encrypted sensor data of the collected data.

20. The wireless stethoscope system of claim 13, wherein the wireless stethoscope is capable of measuring acoustic transmissions including airborne transmission, impact transmission and flanking transmission.

21. The wireless stethoscope of claim 1, further comprising a plastic center piece disposed between the circuit board and the isolation ring.

22. The wireless stethoscope of claim 1, further comprising:
   an isolation unit; and
   a main housing unit; wherein
      the isolation unit is disposed between the circuit board and the main housing unit, and
      the isolation unit is different from the isolation ring and the isolation layer.

\* \* \* \* \*